(12) United States Patent
Homma et al.

(10) Patent No.: US 11,470,283 B2
(45) Date of Patent: Oct. 11, 2022

(54) IMAGE GENERATION APPARATUS, IMAGE DISPLAY APPARATUS, AND IMAGE DISPLAY METHOD

(71) Applicant: OLYMPUS CORPORATION, Hachioji (JP)

(72) Inventors: Hiroyuki Homma, Sagamihara (JP); Akikazu Yachi, Tokorozawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/120,213

(22) Filed: Dec. 13, 2020

(65) Prior Publication Data

US 2021/0099679 A1 Apr. 1, 2021

Related U.S. Application Data

(63) Continuation of application No. PCT/JP2019/006747, filed on Feb. 22, 2019.

(30) Foreign Application Priority Data

Jun. 27, 2018 (JP) .............................. JP2018-121986

(51) Int. Cl.
*H04N 7/18* (2006.01)
*H04N 5/225* (2006.01)
(Continued)

(52) U.S. Cl.
CPC ............. *H04N 7/183* (2013.01); *G06V 10/40* (2022.01); *H04N 5/2254* (2013.01);
(Continued)

(58) Field of Classification Search
CPC .. H04N 7/183; H04N 5/2254; H04N 5/23229; G06V 10/40
See application file for complete search history.

(56) References Cited

U.S. PATENT DOCUMENTS 9,030,543 B2 5/2015 Tsuyuki et al.
9,848,124 B2 12/2017 Iwasaki et al.
(Continued)

FOREIGN PATENT DOCUMENTS

JP  H11197098 A  7/1999
JP  5593004 B2   8/2014
(Continued)

OTHER PUBLICATIONS

Japanese Office Action (and English language translation thereof) dated Aug. 4, 2021 issued in counterpart Japanese Application No. 2020-527193.

(Continued)

*Primary Examiner* — Jonathan R Messmore
(74) *Attorney, Agent, or Firm* — Holtz, Holtz & Volek PC

(57) ABSTRACT

An image generation apparatus includes an objective optical system, an optical-path splitter, an image sensor, and an image processor. Both a first imaging area and a second imaging area are images of a field of view of the objective optical system. An outer edge of the first imaging area and an outer edge of the second imaging area are located at an inner side of a predetermined image pickup area, and an image of the outer edge located in the predetermined image pickup area is captured by the image sensor. The image processor has reference data, and in the image processor, a feature point is extracted on the basis of the imaging area. An amount of shift between the predetermined imaging area and the image sensor is calculated from the feature point and the reference data.

5 Claims, 14 Drawing Sheets

(51) Int. Cl.
  *H04N 5/232* (2006.01)
  *G06V 10/40* (2022.01)
  *A61B 1/00* (2006.01)

(52) U.S. Cl.
  CPC ...... *H04N 5/23229* (2013.01); *A61B 1/00009* (2013.01); *A61B 1/00045* (2013.01); *A61B 1/00121* (2013.01); *H04N 2005/2255* (2013.01)

(56) References Cited

U.S. PATENT DOCUMENTS

| | | | |
|---|---|---|---|
| 10,205,888 | B2 | 2/2019 | Tsuyuki et al. |
| 2012/0321205 | A1* | 12/2012 | Lai .......................... G06V 10/20 382/233 |
| 2014/0176692 | A1 | 6/2014 | Tsuyuki et al. |
| 2016/0088287 | A1* | 3/2016 | Sadi ..................... H04N 13/194 348/43 |
| 2016/0306155 | A1* | 10/2016 | Suzuki ................. G02B 21/365 |
| 2017/0041537 | A1 | 2/2017 | Iwasaki et al. |
| 2017/0187943 | A1 | 6/2017 | Tsuyuki et al. |
| 2019/0295237 | A1* | 9/2019 | Konecky ............ G01N 21/9501 |
| 2020/0326609 | A1* | 10/2020 | Tsubaki ........... H04N 5/232121 |

FOREIGN PATENT DOCUMENTS

| | | |
|---|---|---|
| WO | 2014002740 A1 | 1/2014 |
| WO | 2016043107 A1 | 3/2016 |
| WO | 2016104368 A1 | 6/2016 |
| WO | 2017183371 A1 | 10/2017 |

OTHER PUBLICATIONS

International Preliminary Report on Patentability (IPRP) (and English language translation thereof) dated Dec. 29, 2020 issued in International Application No. PCT/JP2019/006747.

International Search Report (ISR) (and its English-language translation) dated Apr. 23, 2019 issued in International Application No. PCT/JP2019/006747.

Written Opinion dated Apr. 23, 2019 issued in International Application No. PCT/JP2019/006747.

* cited by examiner

IMAGE GENERATION APPARATUS, IMAGE DISPLAY APPARATUS, AND IMAGE DISPLAY METHOD

CROSS-REFERENCE TO RELATED APPLICATION

The present application is a continuation application of PCT/JP2019/006747 filed on Feb. 22, 2019 which is based upon and claims the benefit of priority from Japanese Patent Application No. 2018-121986 filed on Jun. 27, 2018; the entire contents of which are incorporated herein by reference.

BACKGROUND

Technical Field

The present disclosure relates to an image generation apparatus, an image display apparatus, and an image display method.

Description of the Related Art

In recent years, in an apparatus which includes an optical system and an image sensor, making the number of pixels of the image sensor large has been progressing. As the number of pixels of the image sensor becomes large, an area of one pixel becomes small. Therefore, in the optical system, it is necessary to make a resolution high.

For making the resolution of an optical system high, an object-side numerical aperture is made large. However, when the object-side numerical aperture is made large, a depth of field becomes narrow. When the depth of field is narrow, a range which can be observed is limited. When the observation range is narrow, it becomes difficult to observe efficiently.

As an apparatus which widens the depth of field, an endoscope apparatus disclosed in Japanese Patent No. 5593004 Publication is available. In this endoscope apparatus, an optical-path splitter is disposed between an objective optical system and an image sensor. Two optical paths are formed by the optical-path splitter. An optical-path difference arises in the two optical paths. Consequently, two optical images with different focus are formed on the image sensor.

The two optical images with different focus are captured by the image sensor. As a result, two images with different focus are acquired. By combining the two images acquired, an image having a widened depth of field is generated.

Moreover, in the endoscope apparatus, an image correction can be carried out by an image correction processor. In the image correction, relative positions, angles, and magnification of the two images are made substantially same.

In the image correction, correction parameters set in advance are used. Correction amounts of the correction parameters are set in advance in a correction parameter section at the time of shipping from a factory. Moreover, when an endoscope is connected to the image processor, the corresponding parameter is called from the correction parameter section and the correction is carried out.

In an endoscope apparatus, while handling an endoscope, a front-end portion of an endoscope may be subjected to an impact. When the front-end portion is subjected to an impact, a strong force is exerted to at least one of an objective optical system, an optical-path splitter, and an image sensor.

Moreover, cleaning and sterilization of the endoscope are sometimes carried out in a high-temperature and high-humidity environment. In such environment, sometimes an effect of a thermal change reaches the front-end portion. Therefore, when the cleaning and sterilization are carried out, the objective optical system, the optical-path splitter, and the image sensor may be subjected to a thermal force. Furthermore, in cases other than those of having an impact, the cleaning, and the sterilization, sometimes a force is exerted to the front-end portion.

When such force is exerted strongly or repeatedly, a relative shift of a micro order sometimes occurs between the objective optical system and the image sensor, between the optical-path splitter and the image sensor, and between an optical unit and the image sensor. The optical unit includes the objective optical system and the optical-path splitter.

Two optical images with different focus are formed on the image sensor. Therefore, as the abovementioned shift occurs, a relative shift of position occurs between the image sensor and an optical image. The relative shift of position (hereinafter, referred to as 'position shift') has a bad effect at the time of generating a combined image from two images.

An amount of position shift (hereinafter, referred to as the 'amount of shift') can be calculated by providing a reference point to the image sensor or by providing a reference point to the optical system. For instance, when the reference point is provided to the image sensor, the amount of shift can be calculated from a distance from the reference point to a position of the optical image.

When the amount of shift at the time of shipping from the factory is a reference amount, the amount of shift is consistent with the reference amount. Moreover, at the time of shipping from the factory, the image formed by combining the two images is a natural combined image. Therefore, in a state in which the amount of shift is consistent with the reference amount, a natural combined image is generated. Whereas, in a state in which the amount of shift is not consistent with the reference amount, it is not possible to generate a natural combined image.

SUMMARY

An image generation apparatus according to at least some embodiments of the present disclosure includes
an image pickup unit, and
an image processor, wherein
the image pickup unit includes an objective optical system, an optical-path splitter, and an image sensor,
a predetermined imaging area is formed on the image sensor by the optical-path splitter,
the predetermined imaging area includes a first imaging area and a second imaging area,
both the first imaging area and the second imaging area are images of a field of view of the objective optical system,
both an outer edge of the first imaging area and an outer edge of the second imaging area are located at an inner side of a predetermined image pickup area of the image sensor,
an image of the outer edge located in the predetermined image pickup area is captured by the image sensor,
the image processor has reference data,
the reference data includes data indicating a reference point in the predetermined imaging area or data indicating a reference point in the predetermined image pickup area,
in the image processor, a feature point of the first imaging area is extracted on the basis of the outer edge of the first imaging area, and a feature point of the second imaging area is extracted on the basis of the outer edge of the second imaging area, an amount of shift between the predetermined imaging area and the image sensor is calculated from the feature point of the first imaging area, the feature point of the second imaging area, and the reference data, and a display position of a first image acquired from the first imaging area and a display position of a second image acquired from the second imaging area are determined from the amount of shift.

An image display apparatus according to at least some embodiments of the present disclosure includes the abovementioned image generation apparatus, and a display unit.

Moreover, an image display method according to at least some embodiments of the present disclosure includes generating an image of an outer edge of a first imaging area, generating an image of an outer edge of a second imaging area, extracting a feature point of the first imaging area on the basis of the image of the outer edge of the first imaging area, and extracting a feature point of the second imaging area on the basis of the image of the outer edge of the second imaging area, calculating an amount of shift between the predetermined imaging area and the image sensor from the feature point of the first imaging area, the feature point of the second imaging area, and reference data, and determining a display position of a first image acquired from the first imaging area and a display position of a second image acquired from the second imaging area, from the amount of shift, wherein the predetermined imaging area is formed on the image sensor, the predetermined imaging area includes the first imaging area and the second imaging area, the reference data includes data indicating a reference point in the predetermined imaging area or data indicating a reference point in the predetermined image pickup area, and both the first imaging area and the second imaging area are images of a field of view of the objective optical system.

DETAILED DESCRIPTION

Embodiments and examples of an image generation apparatus and image display apparatus will be described below in detail by referring to the accompanying diagrams. However, the present disclosure is not restricted to the embodiments and the examples described below.

An image generation apparatus according to the present embodiment includes an image pickup unit and an image processor. The image pickup unit includes an objective optical system, an optical-path splitter, and an image sensor, and a predetermined imaging area is formed on the image sensor by the optical-path splitter. The predetermined imaging area includes a first imaging area and a second imaging area, and both the first imaging area and the second imaging area are images of a field of view of the objective optical system. Both an outer edge of the first imaging area and an outer edge of the second imaging area are located at an inner side of a predetermined image pickup area of the image sensor, and an image of the outer edge located in the predetermined image pickup area is captured by the image sensor.

The image processor has reference data, and the reference data includes data indicating a reference point in the predetermined imaging area or data indicating a reference point in the predetermined image pickup area. In the image processor, a feature point of the first imaging area is extracted on the basis of the outer edge of the first imaging area and a feature point of the second imaging area is extracted on the basis of the outer edge of the second imaging area. An amount of shift between the predetermined imaging area and the image sensor is calculated from the feature point of the first imaging area, the feature point of the second imaging area, and the reference data. A display position of a first image acquired from the first imaging area and a display position of a second image acquired from the second imaging area are determined from the amount of shift.

An image display apparatus according to the present embodiment includes the image generation apparatus of the present embodiment, and a display unit. Description will be made below by using the image display apparatus of the present embodiment. Advantageous effects in the description below may be achieved even by the image generation apparatus of the present embodiment.

Figure 1:
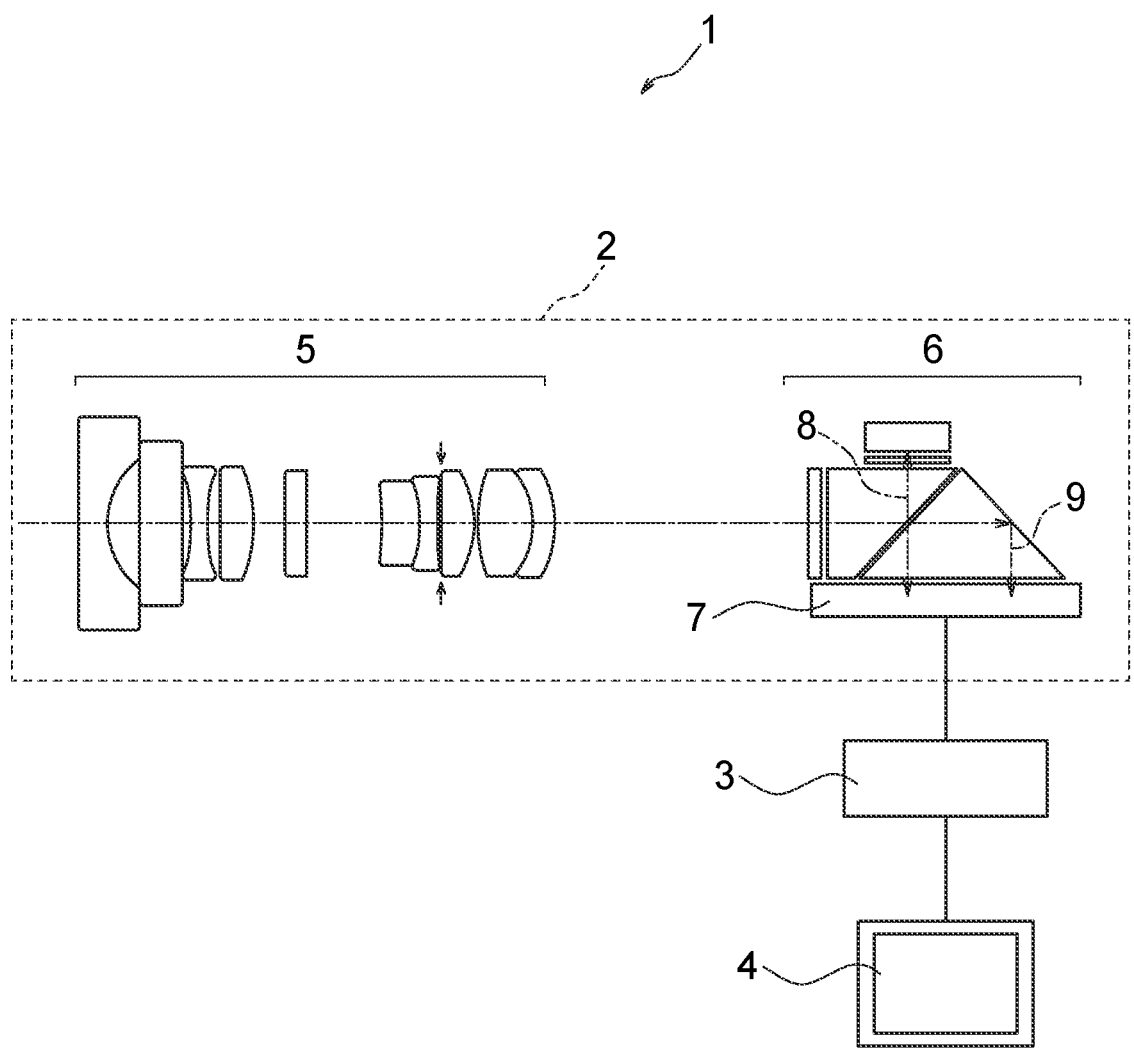
FIG. 1 is a diagram showing an image display apparatus of the present embodiment.

The image display apparatus of the present embodiment is shown in FIG. 1. An image display apparatus 1 includes an image pickup unit 2, an image processor 3, and a display unit 4. The image pickup unit 2 and the image processor 3 form the image generation apparatus. The image pickup unit 2 includes an objective optical system 5, an optical-path splitter 6, and an image sensor 7.

An optical path of the objective optical system 5 is split into a first optical path 8 and a second optical path 9 by the optical-path splitter 6. Moreover, a predetermined imaging area is formed on the image sensor 7 by the optical-path splitter 6.

Figure 2:
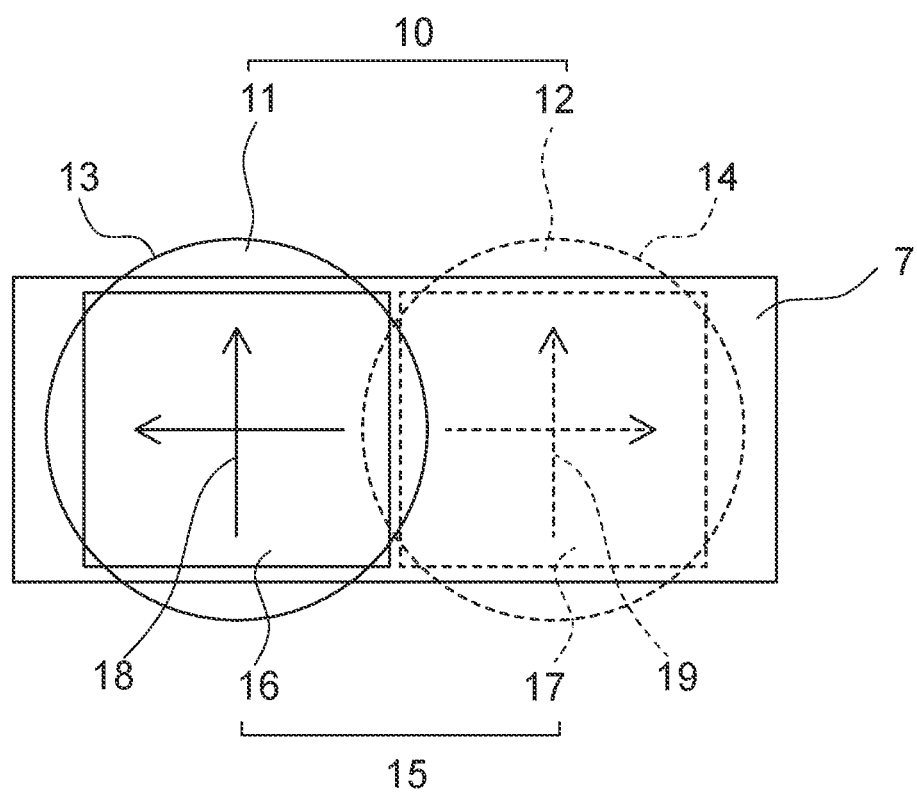
FIG. 2 is a diagram showing appearance of imaging areas and image pickup areas.

Appearance of imaging areas and image pickup areas are shown in FIG. 2. The predetermined imaging area 10 includes a first imaging area 11 and a second imaging area 12. Both the first imaging area 11 and the second imaging area 12 are images of a field of view of the objective optical system 5.

Both an outer edge 13 of the first imaging area 11 and an outer edge 14 of the second imaging area 12 are located at an inner side of a predetermined image pickup area 15 of the image sensor 7. An image of the outer edge located in the predetermined image pickup area 15 is captured by the image sensor 7.

The first imaging area 11 and the second imaging area 12 are formed in parallel on the image sensor 7. The predetermined image pickup area 15 includes a first image pickup area 16 and a second image pickup area 17. The first image pickup area 16 and the second image pickup area 17 are located in parallel on the image sensor 7.

The first imaging area 11 and the first image pickup area 16 are located in the first optical path 8. The second imaging area 12 and the second image pickup area 17 are located in the second optical path 9. An image of the outer edge 13 is captured by the first image pickup area 16. An image of the outer edge 14 is captured by the second image pickup area 17.

A first optical image 18 is formed in the first imaging area 11. A second optical image 19 is formed in the second imaging area 12. In the first optical image 18 and the second optical image 19, one optical image is a mirror image of the other optical image.

Figure 3A:
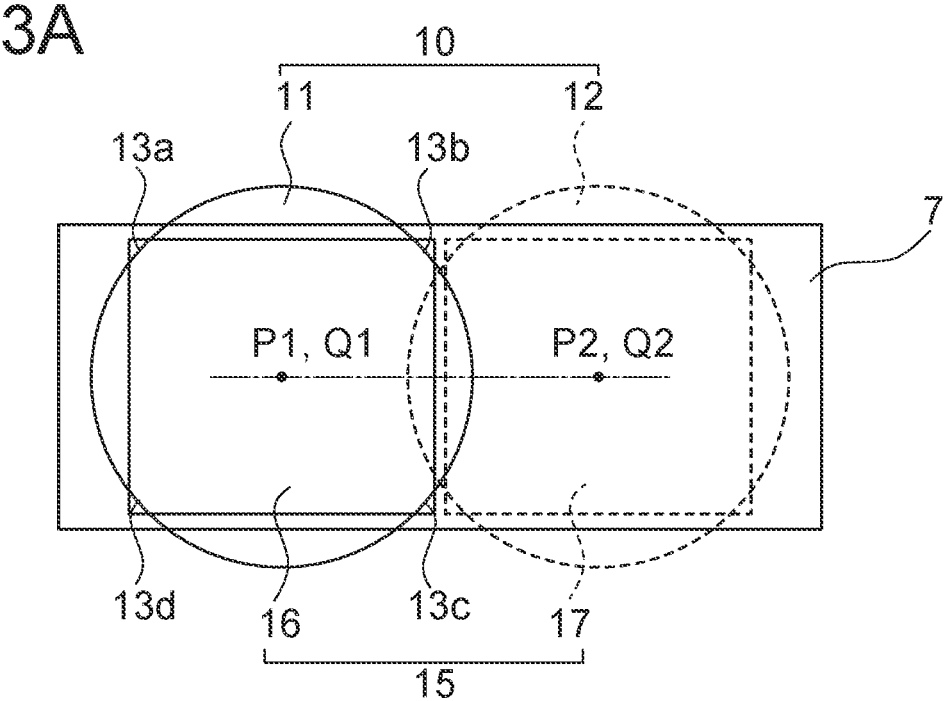
FIG. 3A and FIG. 3B are diagrams showing appearance of the imaging areas and the image pickup areas.
Figure 3B:
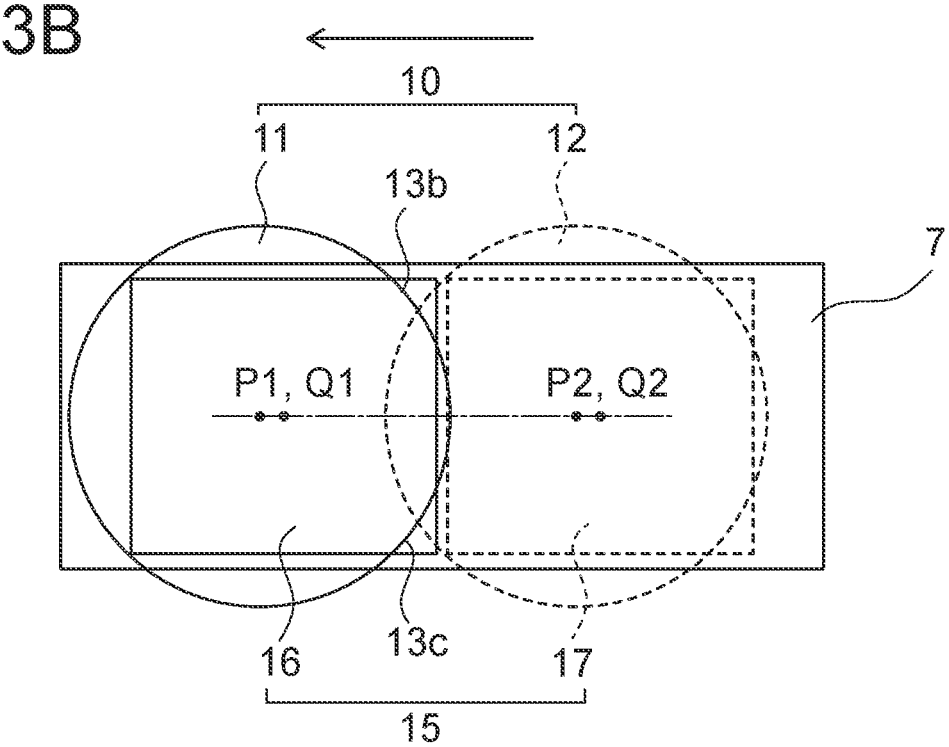

Appearance of the imaging areas and the image pickup areas are shown in FIG. 3A and FIG. 3B. FIG. 3A is a diagram showing an appearance of a reference state. FIG. 3B is a diagram showing an appearance after occurrence of shift.

The reference state will be described below. The reference state includes a state at the time of manufacturing the image pickup unit 2, or a state at the time of shipping the image display apparatus 1 from a factory. Moreover, in a case in which a position shift has occurred after shipping from the factory, a state prior to a state in which the position shift has occurred last time can be considered as the reference state.

For instance, it is assumed that the position shift has occurred three times after shipping from the factory. In this case, the third state becomes the state in which the position shift has occurred last time. Accordingly, a state in which the position shift occurred for the first time or a state in which the position shift occurred for the second time can be considered as the reference state.

As mentioned above, the position shift is a shift in position occurred between the image sensor and the optical image. Moreover, the amount of shift is an amount of shift in position occurred between the image sensor and the optical image. In the image display apparatus 1, the first optical image 18 and the second optical image 19 are formed in the predetermined imaging area 10.

For instance, it is assumed that the image sensor 7 moved in a state in which the objective optical system 5 and the optical-path splitter 6 are stationary. In this case, the first image pickup area 16 and the second image pickup area 17 move. The first optical image 18 is located in the first image pickup area 16. The second optical image 19 is located in the second image pickup area 17. Even when the first image pickup area 16 and the second image pickup area 17 move, the first optical image 18 and the second optical image 19 do not move. In other words, even when the image sensor 7 moves, the predetermined imaging area 10 does not move.

Conversely, it is assumed that at least one of the objective optical system 5 and the optical-path splitter 6 moved in a state in which the image sensor 7 is stationary. In this case, the first optical image 18 and the second optical image 19 move. The first optical image 18 is located in the first image pickup area 16. The second optical image 19 is located in the second image pickup area 17. Even when the first optical image 18 and the second optical image 19 move, the first image pickup area 16 and the second image pickup area 7 do not move. In other words, even when the predetermined imaging area 10 moves, the image sensor 7 does not move.

In such manner, it is possible to replace the position shift occurred between the image sensor and the optical image with a shift in position occurred between the image sensor and the predetermined imaging area.

In the following description, even the shift in position occurred between the image sensor and the predetermined imaging area is referred to as the position shift. Similarly, even an amount of shift in position occurred between the image sensor and the predetermined imaging area is referred to as the amount of shift.

In the image display apparatus 1, the amount of shift is calculated by using the image processor 3. The amount of shift is calculated on the basis of a shift in position occurred between the image sensor 7 and the predetermined imaging area 10. For this, information of a position related to the predetermined imaging area 10 and information of a position related to the image sensor 7 become necessary.

In the image processor 3, as the information of the position related to the predetermined imaging area 10, a feature point P1 of the first imaging area 11 and a feature point P2 of the second imaging area 12 are used. Moreover, as the information of the position related to the image sensor 7, a reference point Q1 in the first image pickup area 16 and a reference point Q2 in the second image pickup area 17 are used.

The feature point P1 can be extracted from the outer edge 13. However, in the first imaging area 11, only an outer edge 13a, an outer edge 13b, an outer edge 13c, and an outer edge 13d are located at four corners of the first imaging area 11.

Each of the outer edge 13a, the outer edge 13b, the outer edge 13c, and the outer edge 13d is a part of the outer edge 13. Therefore, a shape of the overall outer edge 13 is determined by using the outer edge 13a, the outer edge 13b, the outer edge 13c, and the outer edge 13d. When the shape of the overall outer edge 13 is determined, it is possible to determine the feature point P1.

Both the first imaging area 11 and the second imaging area 12 are images of a field of view of the objective optical system 5. A shape of the objective optical system 5 is circular ideally. In this case, a shape of the field of view of the objective optical system 5 becomes circular.

In a state in which the image sensor 7 is disposed ideally, an image pickup surface is perpendicular with respect to an optical axis of the objective optical system 5. However, practically, it is difficult to dispose the image sensor 7 in an ideal state. For instance, due to an assembling error, the image sensor 7 is disposed in a state of being shifted from the ideal state in many cases. In this case, in an image which is acquired by capturing, a shape of an image of the field of view becomes elliptical.

Moreover, a stop and a frame holding a lens are disposed at an interior of the objective optical system 5. The stop and the frame are provided with an opening. In many cases, a shape of the opening is circular. However, a stop and a frame having a noncircular shape are used in some cases. In this case, in an image which is acquired by capturing, a shape of an image of the field of view is not restricted to be circular.

In an objective optical system in which the assembling error is adequately small, the shape of an image of the field of view becomes circular. Moreover, in a case in which a frame having a circular-shaped opening or a stop is used in the objective optical system, the shape of the image of the field of view becomes circular. In a case in which the shape of the image of the field of view is circular, the shape of the first imaging area 11 becomes circular as shown in FIG. 2. Consequently, each of the outer edge 13a, the outer edge 13b, the outer edge 13c, and the outer edge 13d becomes a part of a circumference. Similar is true for the outer edge 14.

Figure 4A:
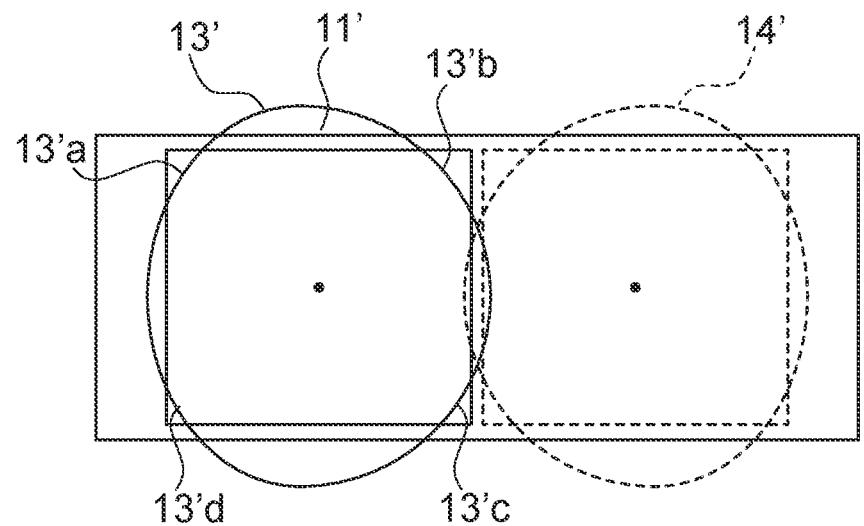
FIG. 4A and FIG. 4B are diagrams showing shapes of an outer edge.
Figure 4B:
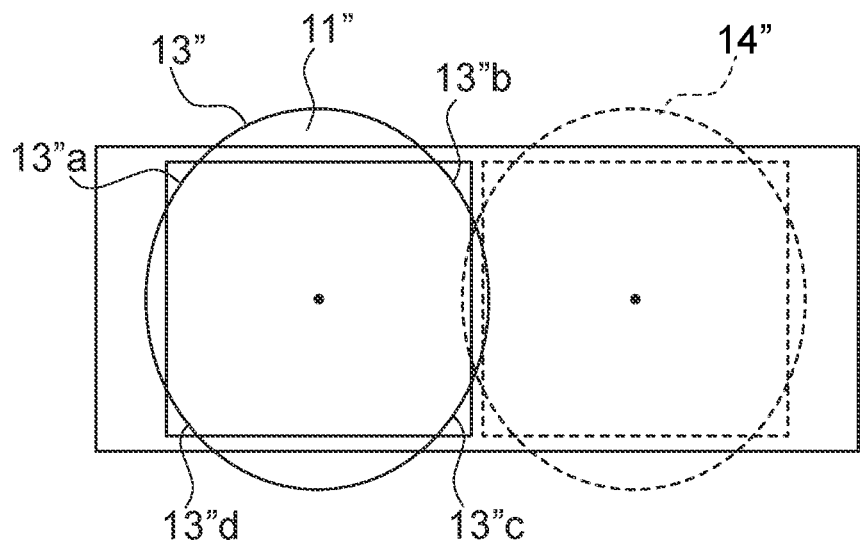

A case in which the shape of the image of the field of view does not become circular will be described below. Shapes of outer edges are shown in FIG. 4A and FIG. 4B. FIG. 4A is a diagram showing a case in which the outer edge is curve. FIG. 4B is a diagram showing a case in which the outer edge is an elliptical circumference.

In the case in which the shape of the image of the field of view does not become circular, a shape of a first imaging area 11' is a shape formed by a curve as shown in FIG. 4A. In this case, an outer edge 13' becomes a curve. Consequently, each of an outer edge 13'a, an outer edge 13'b, an outer edge 13'c, and an outer edge 13'd becomes a part of the curve. Similar is true for an outer edge 14'.

Moreover, in the case in which the shape of the image of the field of view does not become circular, a shape of an imaging area 11" becomes ellipse as shown in FIG. 4B. In this case, an outer edge 13" becomes a circumference of an ellipse. Consequently, each of an outer edge 13"a, an outer edge 13"b, an outer edge 13"c, and an outer edge 13"d becomes a part of the circumference of the ellipse. Similar is true for an outer edge 14".

In a case in which a part of the outer edge 13 is located at an inner side of the first image pickup area 16, for identifying an overall shape of the first imaging area 11, an estimation using the outer edge 13a, the outer edge 13b, the outer edge 13c, and the outer edge 13d is carried out. Similar is true for identifying an overall shape of the first imaging area 11' and for identifying an overall shape of the first imaging area 11". In the estimation, it is possible to use an approximation by a circle, an approximation by an ellipse, and approximation by various other shapes.

In a case in which the outer edge 13 is a curve, a center of gravity of the first imaging area 11 may be made the feature point P1. Moreover, in a case in which the outer edge 13 is a circumference of an ellipse or a circumference of a circle, a center of gravity of the first imaging area 11 or a center of the first imaging area 11 may be made the feature point P1. Similar is true for the second imaging area 12.

In the image processor 3, the amount of shift is calculated from the feature point P1 of the first imaging area 11, the feature point P2 of the second imaging area 12, and the reference data.

The reference data is data indicating a reference point in the predetermined image pickup area 15. The predetermined image pickup area 15 includes the first image pickup area 16 and the second image pickup area 17. Accordingly, it is possible to use the reference point Q1 and the reference point Q2 as the reference data.

For instance, a center of the first image pickup area 16 may be made the reference point Q1. For instance, a center of the second image pickup area 17 may be made the reference point Q2.

In the reference state, a position of the feature point P1 and a position of the reference point Q1 coincide. Moreover, a position of the feature point P2 and a position of the reference point Q2 coincide. The amount of shift ΔPQ is a difference between the position of the feature point P1 and the reference point Q1 or a difference between the position of the feature point P2 and the reference point Q2.

In the reference state, both the difference between the position of the feature point P1 and the position of the reference point Q1 as well as the difference between the position of the feature point P2 and the position of the reference point Q2 are zero. Accordingly, in the reference state, the amount of shift ΔPQ is zero.

As mentioned above, it is possible to set the amount of shift at the time of shipping from the factory in the reference data. Amount that can be set in the reference data is not restricted to the amount of shift at the time of shipping from the factory. It is possible to set any amount of shift in the reference data, if it is an amount of shift in the reference state. As mentioned above, in the reference state, the amount of shift ΔPQ is zero. Therefore, the reference data Δref also becomes zero.

However, in manufacturing of the image pickup unit 2, it is difficult to make the manufacturing error zero. Therefore, practically, it is difficult to make the amount of shift zero. As just described, a value of the reference data need not be zero.

A case in which the shift occurred will be described below. It is assumed that a position shift occurred in the image display apparatus 1 due to the image display apparatus 1 in the reference state being subjected to an impact. In FIG. 3B, the predetermined imaging area 10 shifts in a direction of arrow with respect to the image sensor 7.

In this case, the first imaging area 11 and the second imaging area 12 also move in the direction of arrow. Therefore, it is necessary to identify the positions of the feature points after the shift.

As shown in FIG. 3B, even after an occurrence of shift, in the first imaging area 11, the outer edge 13b and the outer edge 13c are located at the inner side of the first imaging area 11. Accordingly, for identifying the overall shape of the first imaging area 11 after the shift, estimation using the outer edge 13b and the outer edge 13c is carried out. Once it is possible to identity the overall shape of the first imaging area 11 after the shift, it is possible to identify the feature point P1 after the shift. Similar is true for the feature point P2.

As mentioned above, in the reference state, the shape of the first imaging area 11 is already known. Accordingly, the shape of the first imaging area 11 obtained in the reference state may be use for identifying the overall shape of the first imaging area 11 after the shift. Moreover, the shape of the first imaging area 11 obtained in the reference state may be used for identifying the feature point P1 after the shift. Similar is true for the feature point P2.

After the occurrence of shift, the position of the feature point P1 and the position of the reference point Q1 do not coincide. Moreover, also the position of the feature point P2 and the position of the reference point Q2 do not coincide. The amount of shift ΔPQ is a difference between the position of the feature point P1 and the position of the reference point Q1 or a difference between the position of the feature point P2 and the position of the reference point Q2.

Neither of the difference between the position of the feature point P1 and the position of the reference point Q1 and the difference between the position of the feature point P2 and the position of the reference point Q2 is zero. Accordingly, after the occurrence of shift, the amount of shift ΔPQ is not zero. By subtracting a reference amount Δref from the amount of shift ΔPQ, it is possible to calculate the amount of shift ΔPQ after the occurrence of shift.

In a case of the shift, a direction of movement of the feature point P1 with respect to the reference point Q1 and a direction of movement of the feature point P2 with respect to the reference point Q2 are same. Moreover, an amount of movement of the feature point P1 and an amount of movement of the feature point P2 are same. Accordingly, it is possible to calculate the amount of shift ΔPQ by using only one of the feature point P1 and the feature point P2.

Figure 5A:
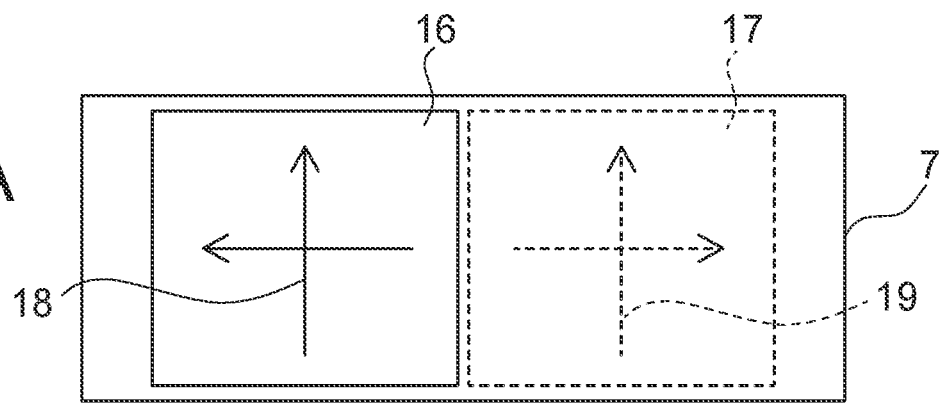
FIG. 5A and FIG. 5B are diagrams showing appearance of optical images and the image pickup areas.
Figure 5B:
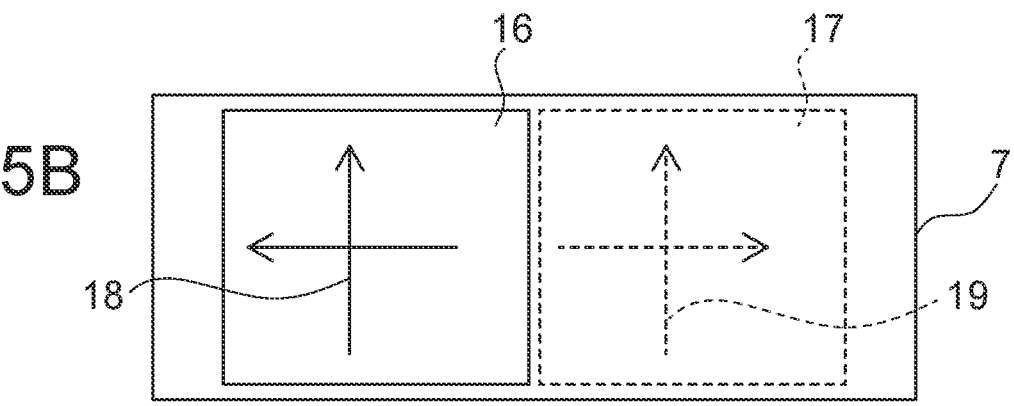

The optical images and the image pickup areas are shown in FIG. 5A and FIG. 5B. FIG. 5A is a diagram showing an appearance of the reference state. FIG. 5B is a diagram showing an appearance after occurrence of shift.

When the shift occurs in the reference state, the first optical image 18 and the second optical image 19 move from positions in the reference state. At this time, the first optical image 18 and the second optical image 19 shift in the same direction.

Figure 6A:
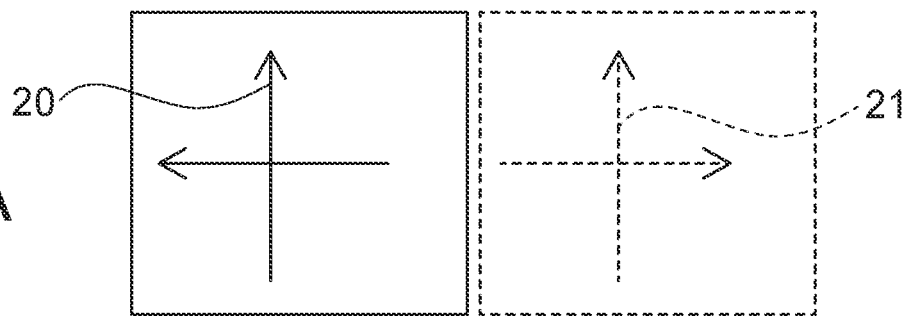
FIG. 6A, FIG. 6B, and FIG. 6C are diagrams showing appearance of an image of the optical images.
Figure 6B:
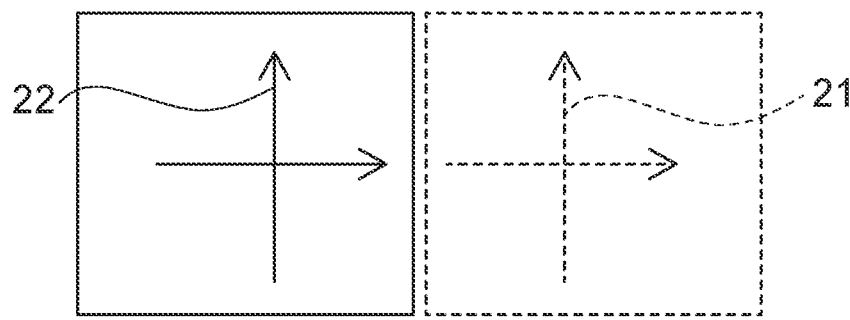
Figure 6C:
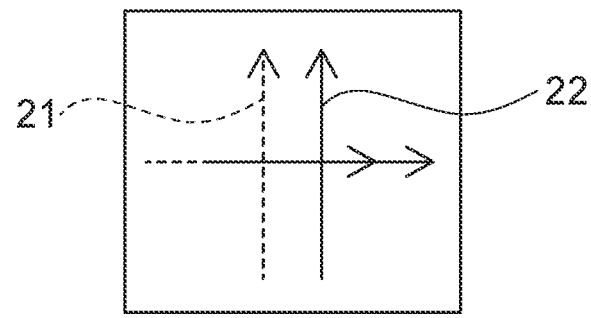

An image of the optical images is shown in FIG. 6A, FIG. 6B, and FIG. 6C. FIG. 6A is a diagram showing an appearance before inverting an image. FIG. 6B is a diagram showing an appearance after inverting the image. FIG. 6C is a diagram showing an appearance after combining the two images.

In a state of the shift occurred, the first optical image 18 and the second optical image 19 are captured. By capturing the images, a first image 20 and a second image 21 are acquired as shown in FIG. 6A. In the first image 20 and the second image 21, one image is a mirror image of the other image. Therefore, it is not possible to combine the first image 20 and the second image 21.

And so, an inverted image 22 as shown in FIG. 6B is generated. The inverted image 22 is an image of the first image 20 inverted in a left-right direction. Accordingly, it is possible to combine the inverted image 22 and the second image 21.

However, in the inverted image 22, a direction of shift becomes opposite to that of the first image 20. In this case, as shown in FIG. 6C, in the combined image, the inverted image 22 and the second image 21 do not overlap. Consequently, an unnatural image is generated.

In the image display apparatus 1, the amount of shift ΔPQ is calculated in the image processor 3. Therefore, from the amount of shift ΔPQ, it is possible to determine a display position of the inverted image 22 and a display position of the second image 21. In other words, it is possible to overlap the inverted image 22 and the second image 21. As a result, it is possible to generate a natural combined image.

Figure 7A:
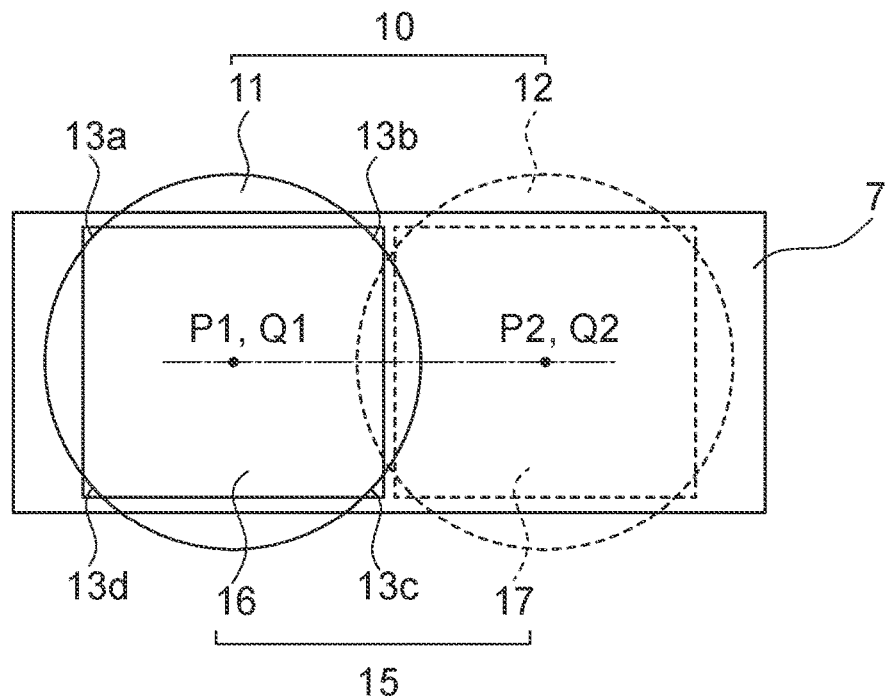
FIG. 7A and FIG. 7B are diagrams showing appearance of the imaging areas and the image pickup areas.
Figure 7B:
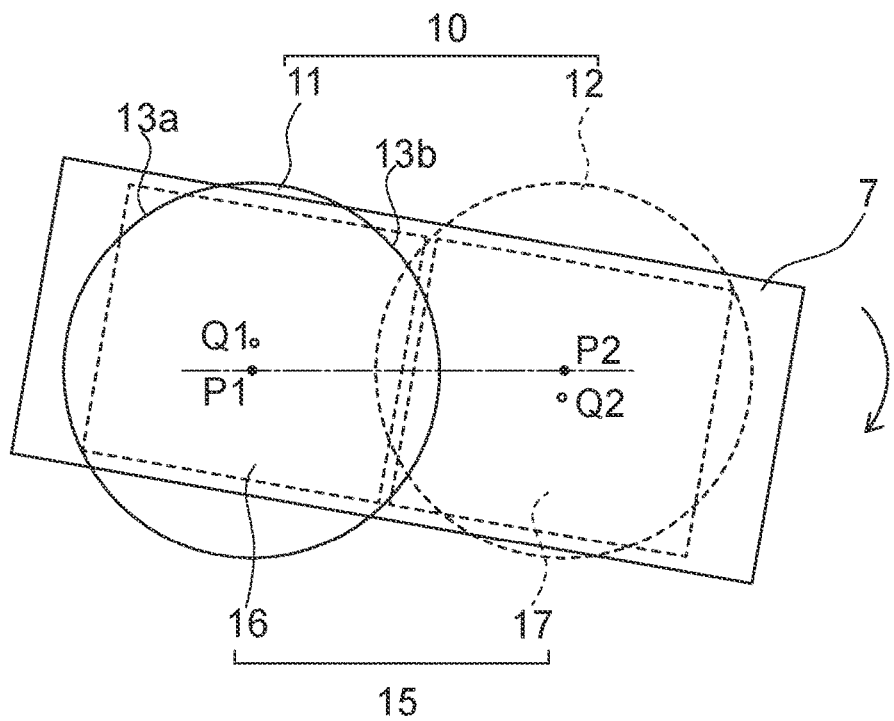

Appearance of the imaging areas and the image pickup areas are shown in FIG. 7A and FIG. 7B. FIG. 7A is a diagram showing appearance of the reference state. FIG. 7B is diagram showing appearance of after occurrence of rotation. Description of the reference state is omitted.

A case in which the rotation occurred will be described below. It is assumed that the position shift occurred in the image display apparatus 1 due to the image display apparatus 1 in the reference state being subjected to an impact. In FIG. 7B, the image sensor 7 rotates in a direction of an arrow with respect to the predetermined imaging area 10.

In this case, due to the rotation, the reference point Q1 and the reference point Q2 rotate in the direction of the arrow. Whereas, the first imaging area 11 and the second imaging area 12 do not rotate. Therefore, it is possible to make the feature point P1 and the feature point P2 as the reference.

However, when the image sensor 7 is made the reference, accordingly, the first imaging area 11 and the second imaging area 12 rotated. In this case, a position of the feature point P1 and a position of the feature point P2 after rotating, are identified.

As mentioned above, the shape of the first imaging area 11 has already been known in the reference state. As shown in FIG. 7B, even after occurrence of rotation, in the first imaging area 11, the outer edge 13a and the outer edge 13b are located at the inner side of the first imaging area 11. Therefore, for identifying the overall shape of the first imaging area 11 after the rotation, the estimation is carried out by using the outer edge 13a and the outer edge 13b. When it is possible to identify the overall shape of the first image pickup area 11 after the rotation, it is possible to identify the feature point P1 after the rotation. Similar is true for the feature point P2.

As mentioned above, in the reference state, the shape of the first imaging area 11 is already known. Accordingly, the shape of the first imaging area 11 obtained in the reference state may be used for identifying the overall shape of the first imaging area 11 after the rotation. Moreover, the shape of the first imaging area 11 obtained in the reference state may be used for identifying the feature point P1 after the rotation. Similar is true for the feature point P2.

After the occurrence of rotation, the position of the feature point P1 and the position of the reference point Q1 do not coincide. Moreover, also the position of the feature point P2 and the position of the reference point do not coincide. The amount of shift ΔPQ is a difference between the position of the feature point P1 and the position of the reference point Q1 or a difference between the position of the feature point P2 and the position of the reference point Q2.

Neither of the difference between the position of the feature point P1 and the position of the reference point Q1 and the difference between the position of the feature point P2 and the position of the reference point Q1 is zero. Accordingly, after the occurrence of rotation, the amount of shift ΔPQ is not zero. By subtracting the reference amount Δref from the amount of shift ΔPQ, it is possible to calculate the amount of shift ΔPQ after the occurrence of rotation.

The shift of the position of the feature point P1 and the position of the reference point Q1 may occur even due to the shift. Therefore, when only the feature point P1 is taken into account, it is not possible to distinguish whether the misalignment has occurred due to the rotation or has occurred due to the shift.

In the image processor 3, the difference between the position of the feature point P2 and the position of the referenced point Q2 is also calculated. Therefore, when the reference point Q2 is taken into account, in a case of the rotation, a direction of movement of the feature point P2 with respect to the reference point Q2 is opposite to a direction of movement of the feature point P1 with respect to the reference point Q. Whereas, in a case of the shift, as mentioned above, the direction of movement of the feature point P2 with respect to the reference point Q2 is same as the direction of movement of the feature point P1 with respect to the reference point Q1.

Therefore, by calculating the difference between the position of the feature point P2 and the position of the reference point Q2, it is possible to distinguish whether the shift of the positions of the feature point P1 and the reference point Q1 has occurred due to the rotation or has occurred due to the shift.

When the shift occurs in the reference state, the first optical image 18 and the second optical image 19 move from the positions in the reference state as shown in FIG. 5B. Accordingly, by using the optical images, it is possible to calculate the amount of shift. In this case, the feature points are set for the optical images. Therefore, for calculation of the amount of shift, it is necessary to use the same optical images every time.

For instance, it is assumed that the amount of shift at the time of shipping from the factory has been used for setting the reference data. It is assumed that an object used for calculating the amount of shift is a reference object. In a case of calculating the amount of shift after shipping from the factory, it is necessary to use the reference object or a precise replica of the reference object.

Moreover, with respect to a correlation of the object and the objective optical system, it is necessary to reproduce faithfully the correlation at the time of shipping from the factory. The correlation refers to a distance between the object and the objective optical system, relative positions of the object and the objective optical system on a plane orthogonal to an optical axis, and a direction of the objective optical system with respect to the object.

The feature points in the optical images do not indicate directly the position of the objective optical system. Therefore, in a case of calculating the amount of shift by using the optical images, various constraints are imposed.

Whereas, in the image display apparatus 1, the amount of shift is calculated by using the predetermined imaging area 10. The predetermined image area 10 is an image of the field of view of the objective optical system 5. The field of view is determined by the position of the objective optical system 5. Therefore, the image of the field of view, or in other words, the predetermined imaging area 10 is also determined by the position of the objective optical system 5.

As just described, the predetermined imaging area 10 indicates directly the position of the objective optical system 5. Moreover, the feature points are set in the predetermined imaging area 10. Accordingly, in the image display apparatus 1, it is possible to calculate the amount of shift easily.

In the image display apparatus 1, it is possible to position the entire outer edge 13 of the first imaging area 11 within the predetermined image pickup area 15. Moreover, it is possible to position the entire outer edge 14 of the second imaging area 12 within the predetermined image pickup area 15.

Moreover, in the image display apparatus 1, it is possible to position a part of the outer edge 13 of the first imaging area 11 within the predetermined image pickup area 15. Furthermore, it is possible to position a part of the outer edge 14 of the second imaging area 12 within the predetermined image pickup area 15.

Figure 8A:
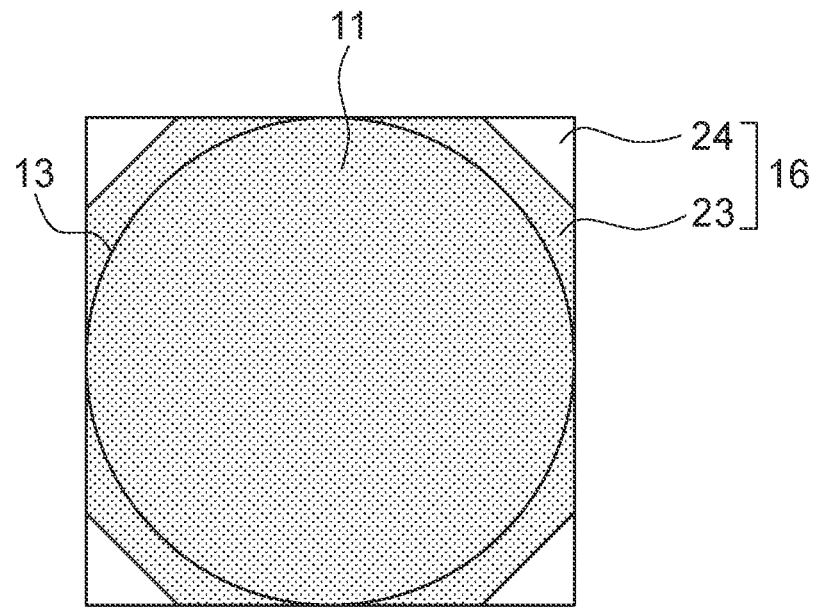
FIG. 8A and FIG. 8B are diagrams showing appearance of the image pickup area and an area for display.
Figure 8B:
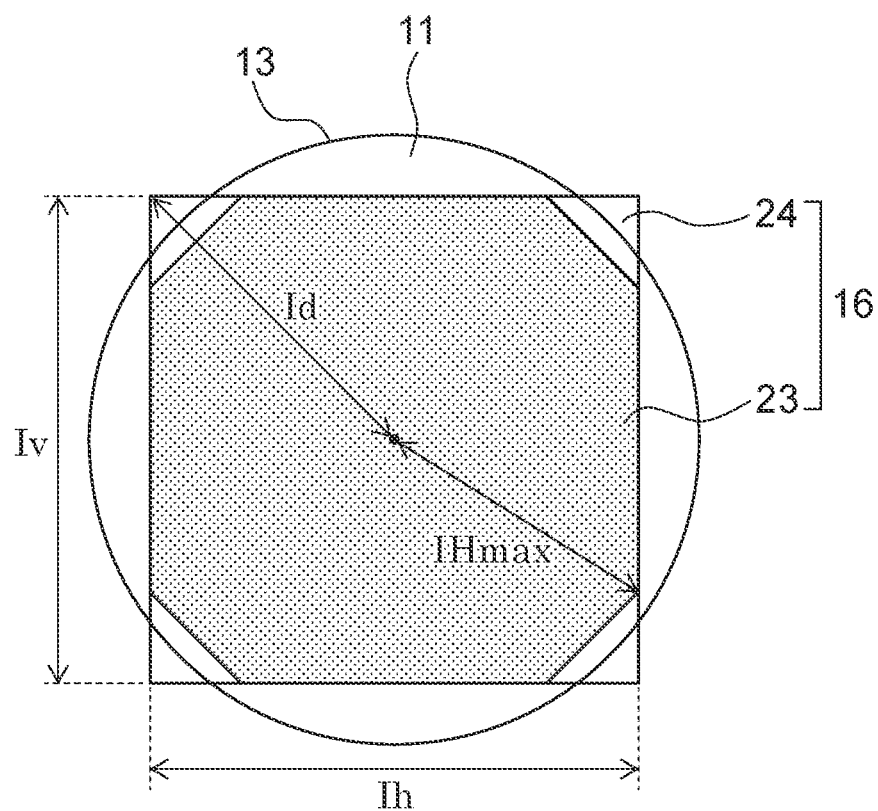

Appearance of the image pickup area and an area for display are shown in FIG. 8A and FIG. 8B. FIG. 8A is diagram showing an appearance in which the entire outer edge is located within the image pickup area. FIG. 8B is a diagram showing an appearance in which a part of the outer edge is located within the image pickup area.

As mentioned above, both the outer edge 13 of the first imaging area 11 and the outer edge 14 of the second imaging area 12 are located at the inner side of the predetermined image pickup area 15. In the first imaging area 11, the outer edge 13 is located at the inner side of the first image pickup area 16. In the second imaging area 12, the outer edge 14 is located at the inner side of the second image pickup area 17.

The predetermined image pickup area 15 includes the first image pickup area 16 and the second image pickup area 17. Here, description will be made by using the first image pickup area 16.

The first image pickup area 16 includes an area for display 23 and an area 24. The area for display 23 is located at the inner side of the first image pickup area 16, and is an image pickup area used for displaying the first image. A shape of the area for display 23 is an octagonal shape. A shape of the area 24 is a triangular shape. The area 24 is located at four corners of the first image pickup area 16.

In FIG. 8A, the entire outer edge 13 is located at the inner side of the first image pickup area 16. As mentioned above, the feature point is determined by using the shape of the overall outer edge 13. In FIG. 8A, the shape of the overall outer edge 13 being evident, it is not necessary to estimate the shape of the overall outer edge 13. Consequently, it is possible to determine the feature point accurately.

However, an optical image is formed at the inner side of the outer edge 13. Therefore, it is not possible to use a part of the area for display 23 for displaying the optical image.

On the other hand, in FIG. 8B, a part of the outer edge 13 is located at the inner side of the first image pickup area 16. Even in this case, an optical image is formed at the inner side of the outer edge 13. Here, the entire area for display 23 is located at the inner side of the outer edge 13. Therefore, it is possible to use the entire area for display 23 for displaying the optical image.

However, as mentioned above, the feature point is determined by using the shape of the overall outer edge 13. In FIG. 8B, the shape of the overall outer edge 13 is not evident. Therefore, the shape of the overall outer edge 13 is to be estimated.

In the image display apparatus according to the present embodiment, it is preferable that the predetermined image pickup area include a first image pickup area and a second image pickup area, both the first image pickup area and the second image pickup area be rectangular-shaped areas, the first imaging area be located in the first image pickup area, the second imaging area be located in the second image pickup area, and following conditional expressions (1) and (2) are satisfied:

$$1 < f/IH\max < 1.2 \tag{1}$$

$$0.8 < f/Id < 0.98 \tag{2}$$

where, f denotes a focal length of the objective optical system,

IHmax denotes a maximum length of an area for display, $$Id = \{(Iv/2)^2 + (Ih/2)^2\}^{1/2}, \text{ where}$$

Iv denotes a length in a longitudinal direction of the rectangular-shaped area,

Ih denotes a length in a transverse direction of the rectangular-shaped area, the area for display is an image pickup area located at an inner side of the first image pickup area and is used for display of the first image, or an image pickup area located at an inner side of the second image pickup area and is used for display of the second image, and the maximum length is a maximum distance of distances from a center of the area for display to an outer edge of the area for display.

By satisfying conditional expressions (1) and (2), even by using a small-size image sensor, it is possible to position the outer edge of the imaging area at the inner side of the image pickup area as well as to position the entire area for display at the inner side of the imaging area. Consequently, it is possible to use the entire area for display for displaying the optical image as well as to calculate the amount of shift.

For example, it is possible to make a value of IHmax an image height corresponding to a predetermined light ray. The predetermined light ray is a light ray corresponding to a half angle of view at which a total reflection occurs. It is possible to make the half angle of view at which the total reflection occurs, 85 degrees for example.

In the image display apparatus according to the present embodiment, it is preferable that an image including the outer edge located in the predetermined image pickup area include an inner-side area and an outer-side area, the inner-side area be located at the inner side of the outer edge located in the predetermined image pickup area, the outer-side area be located at the outer side of the outer edge located in the predetermined image pickup area, the inner-side area include an area having uniform brightness, and the area having uniform brightness make a contact with the outer edge located in the predetermined image pickup area.

As mentioned above, in the calculation of the amount of shift, the feature point and the reference point are used. It is possible to extract the feature point from the outer edge of the imaging area. Therefore, it is necessary to identify the outer edge of the imaging area.

The outer edge of the imaging area is located in the predetermined image pickup area 15. Accordingly, an image of the outer edge of the imaging area is captured by the image sensor 7. Consequently, it is possible to acquire an image which includes the outer edge located in the predetermined image pickup area.

Figure 9:
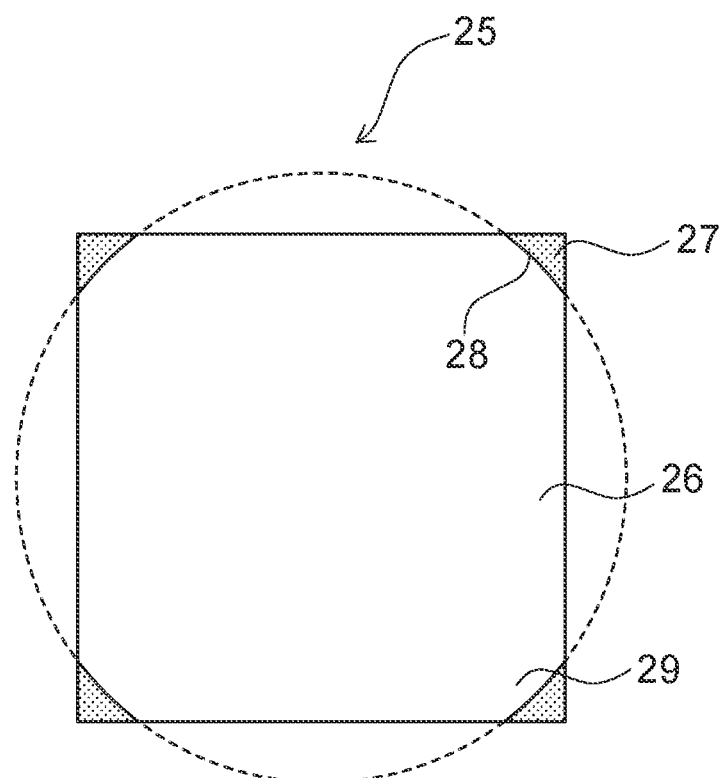
FIG. 9 is a diagram showing an image including the outer edge.

The image which includes the outer edge located in the predetermined image pickup area will be described. An image including the outer edge is shown in FIG. 9. In FIG. 9, for reference, an entire outer edge located in the predetermined image pickup area is indicated by a dashed line.

An image 25 which includes the outer edge located in the predetermined image pickup area (hereinafter, referred to as the 'image 25') includes an inner-side area 26 and an outer-side area 27. The inner-side area 26 is located at an inner side of an outer edge 28 located in the predetermined image pickup area (hereinafter, referred to as the 'outer edge 28'). The outer-side area 27 is located at an outer side of the outer edge 28.

The inner-side area 26 includes an area 29 having uniform brightness (hereinafter, referred to as the 'area 29'). The area 29 will be described later.

The predetermined image pickup area includes the first image pickup area 16 and the second image pickup area 17. Therefore, the image 25 can be deemed as an image which includes the outer edge 13 located in the first image pickup area 16 or an image which includes the outer edge 14 located in the second image pickup area 17.

As shown in FIG. 2, the outer edge 13 is located at an inner side of the first image pickup area 16. The outer edge 14 is located at an inner side of the second image pickup area 17. Accordingly, by capture in the first image pickup area 16 and by capture in the second image pickup area 17, it is possible to acquire an image which includes the outer edge 13 and an image which includes the outer edge 14. It is possible to identify the outer edge 13 and the outer edge 14 from the images acquired.

The outer edge located in the predetermined image pickup area is an outer edge of the predetermined imaging area. The predetermined imaging area is an image of the field of view. Light from an outer side of the field of view is not incident on the objective optical system. Therefore, the light does not reach an outer side of the image of the field of view. In this case, for the image 25, a value of pixel in the outer-side area 27 becomes zero.

On the other hand, light from the inner side of the field of view is incident on the objective optical system. Accordingly, light reaches an inner side of the image of the field of view. In this case, in the image 25, the value of pixel in the inner-side area 26 becomes a value corresponding to a brightness of the incident light.

Therefore, an arrangement is made so that in the inner-side area 26, the value of pixel becomes larger than zero. By making such arrangement, it is possible to make the outer edge 28 clear. As a difference between the value of pixel in the inner-side area 26 and the value of pixel in the outer-side area 27 becomes larger, the outer edge 28 becomes clearer.

For making the value of pixel in the inner-side area 26 large, the inner side of the field of view is to be filled with light. A method for filling the inner side of the field of view with light will be described by using a specific example of the image display apparatus.

Figure 10:
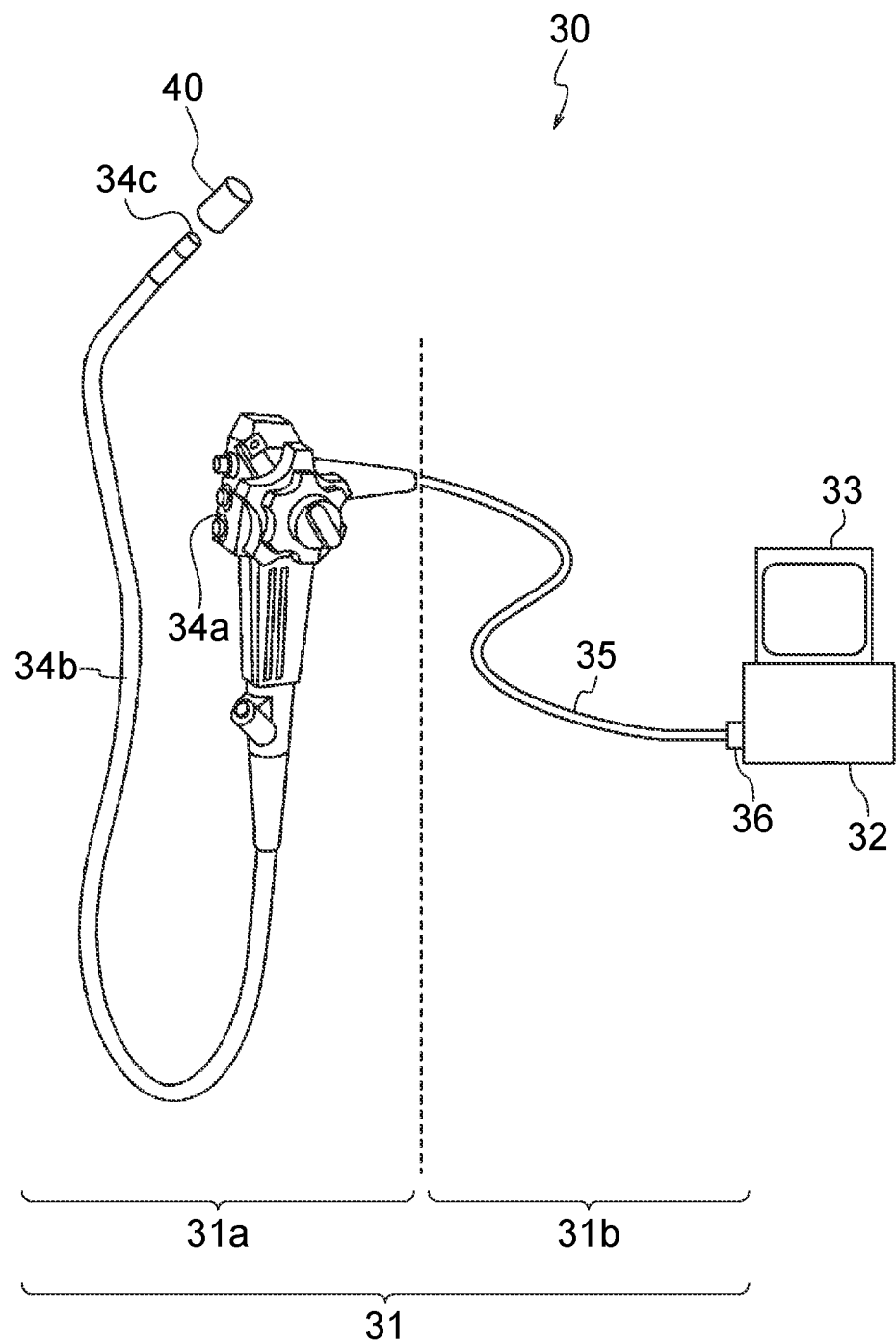
FIG. 10 is a diagram showing a specific example of an image display apparatus.

The specific example of the image display apparatus is shown in FIG. 10. In this example, the image display apparatus is an endoscope system. FIG. 10 shows a schematic configuration of the endoscope system.

An endoscope system 30 is an observation system in which an electronic endoscope is used. The endoscope system 30 includes an electronic endoscope 31 and an image processor 32. The electronic endoscope 31 includes a scope section 31a and a connecting chord section 31b. Moreover, a display unit 33 is connected to the image processor 32.

The scope section 31a is broadly divided into an operating portion 34a and an insertion portion 34b. The insertion portion 34b is long and slender, and is insertable inside a body cavity of a patient. Moreover, the insertion portion 34b includes a flexible member. An observer can carry out various operations by an angle knob etc. provided to the operating portion 34a.

Moreover, the connecting chord portion 31b is extended from the operating portion 34a. The connecting chord portion 31b includes a universal chord 35. The universal chord 35 is connected to the image processor 32 via a connector 36.

The universal chord 35 is used for transmission and reception of various signals. Examples of various signals are a power-supply voltage signal and a CCD (Charge Couple Device) drive signal. These signals are transmitted from a power-supply unit and a video processor to the scope section 31a. Moreover, an example of various signals is a video signal. The video signal is transmitted from the scope section 31a to the video processor.

Peripheral equipment such as an image recording apparatus etc. not shown in the diagram is connectable to the video processor inside the image processor 32. The video processor executes a signal processing on the video signal from the scope section 31a. On the basis of the video signal, an endoscopic image is displayed on a display screen of the display unit 33.

A front-end portion 34c is provided to a front end of the insertion portion 34b. In FIG. 10, a structure 40 is shown near the front-end portion 34c.

Figure 11A:
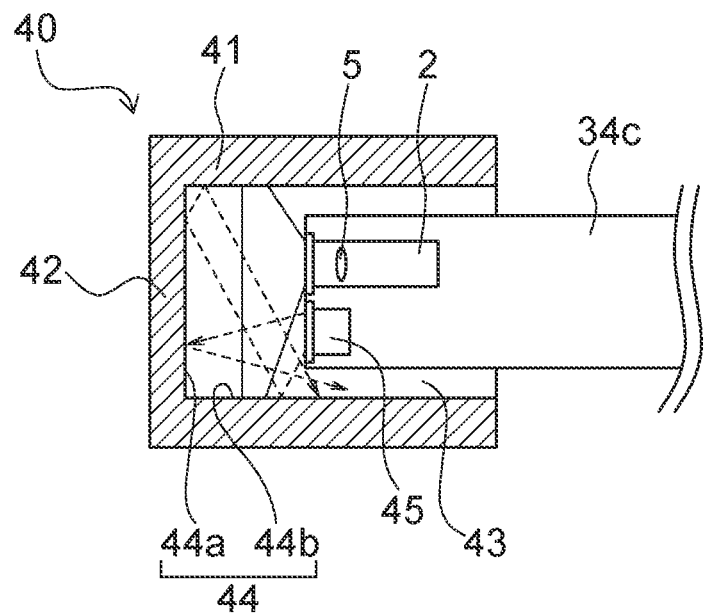
FIG. 11A and FIG. 11B are diagrams showing a structure.
Figure 11B:
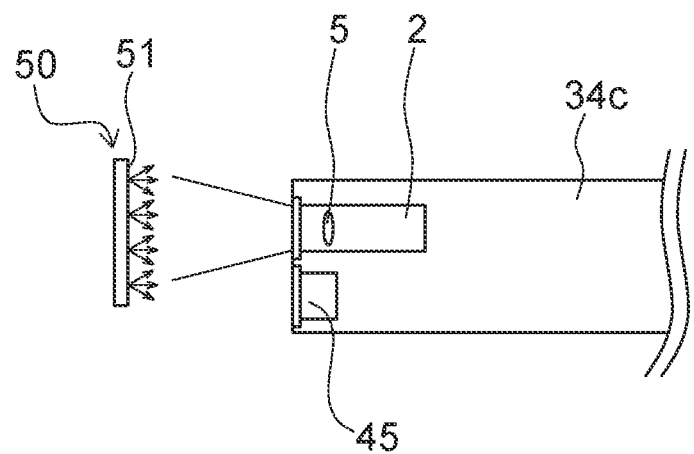

Structures are shown in FIG. 11A and FIG. 11B. FIG. 11A is a diagram showing a first example of the structure. FIG. 11B is a diagram showing a second example of the structure.

The structure of the first example will be described below. The structure 40 in the first example includes a circular cylindrical portion 41 and a flat portion 42. The flat portion 42 is located at one end of the circular cylindrical portion 41. A space 43 is formed at an interior of the structure 40 by the circular cylindrical portion 41 and the flat portion 42. An inner surface 44 is located on a space 43 side.

The front-end portion 34c is inserted into the space 43. The image pickup unit 2 and an illuminating optical system 45 are disposed in the front-end portion 34c.

Illumination light emerges from the illuminating optical system 45. The front-end portion 34c is facing the inner surface 44 of the structure 40. Consequently, the illumination light is irradiated to an inner-bottom surface 44a and an inner-side surface 44b. At this time, the illumination light is repeatedly reflected by the inner surfaced 44. As a result, the inner surface 44 is illuminated with uniform brightness. A brightness distribution is not to be non-uniform at the inner surface 44. Therefore, the brightness distribution is not required to be perfectly uniform. It is more preferable that the brightness distribution be substantially uniform.

The inner surface 44 is formed by the same material which forms the flat portion 42. However, the inner surface 44 may have been provided with a coating agent such as a reflective film. When such arrangement is made, the uniformity of light increases. The illumination light irradiated to the inner surface 44 is reflected at the inner surface 44. Light reflected at the inner surface 44 is incident on the objective optical system 5.

In the structure 40, the illumination light is irradiated to a range wider than the field of view of the objective optical system 5. Accordingly, light is incident on the objective optical system from the overall field of view. As a result, a bright imaging area is formed in the image pickup area.

In the structure 40, the circular cylindrical portion 41 and the flat portion 42 are used. However, the light reflected at the inner surface 44 is the light incident on the objective optical system 5. Therefore, the inner surface 44 may be made a spherical surface and not a circular cylinder.

The structure of the second example will be described below. In the flat portion 42, the illumination light is reflected at the inner surface 44. However, the flat portion 42 may be made a light-emitting surface. A structure 50 of the second example includes a light-emitting surface 51. The light-emitting surface 51 may have an area having substantially uniform brightness distribution.

As mentioned above, the inner surface 44 is illuminated with uniform brightness. In this case, the brightness in the imaging area also becomes uniform. The inner-side area 26 reflects the brightness of the imaging area. As shown in FIG. 9, the inner-side area 26 includes the area 29. In the area 29, the brightness distribution is not required to be perfectly uniform. The brightness distribution may be made substantially uniform.

The area 29 is distributed over the entire inner-surface area 26. The inner-surface area 26 makes a contact with the outer edge 28. Accordingly, in the image 25, the area 29 makes a contact with the outer edge 28 at four locations.

The outer-side area 27 is an area corresponding to the outer side of the field of view. As mentioned above, the light from the outer side of the field of view is not incident on the objective optical system 5. Consequently, the value of pixel in the outer-side area 27 becomes zero.

On the other hand, the inner-side area 26 is an area corresponding to the inner side of the field of view. At the inner side of the field of view, light reflected at the inner surface 44 is incident on the objective optical system 5. In this case, the value of pixel in the inner-side area 26 does not become zero. Consequently, the value of pixel in the area 29 also does not become zero.

The area 29 and the outer-side area 27 make a contact with the outer edge 28. The value of pixel in the area 29 is larger than zero, and the value of pixel in the outer-side area 27 is zero. In this case, it is possible to distinguish clearly the area 29 and the outer-side area 27. As a result, it is possible to identify the outer edge 28 clearly. By the outer edge 28 being identified, it is possible to extract the feature point. From the feature point and the reference data, it is possible to calculate the amount of shift.

In the image 25, the entire inner-surface area 26 is an area having uniform brightness. However, the area having uniform brightness may be a part of the inner-side area 26.

Figure 12A:
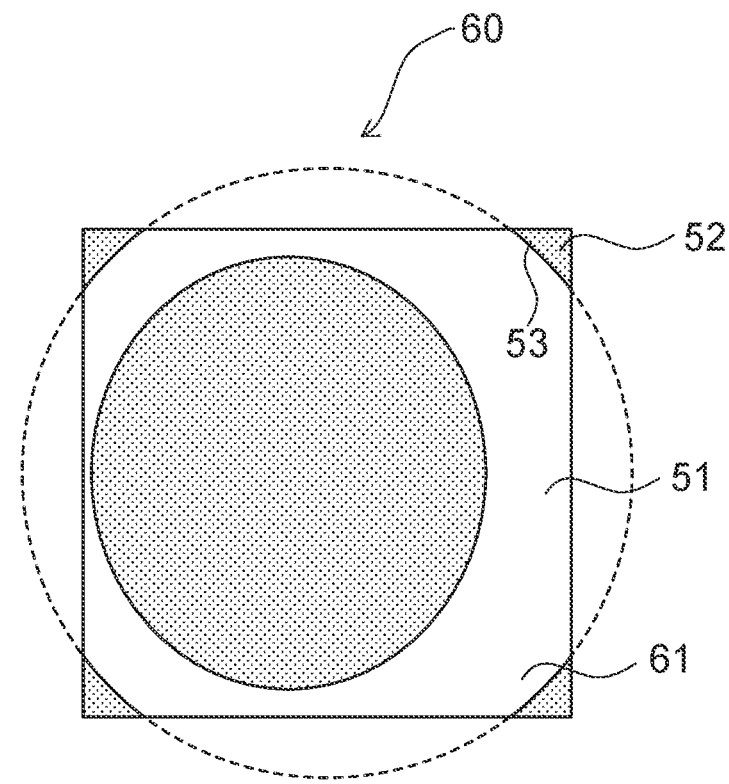
FIG. 12A and FIG. 12B are diagrams showing examples of an area having uniform brightness.
Figure 12B:
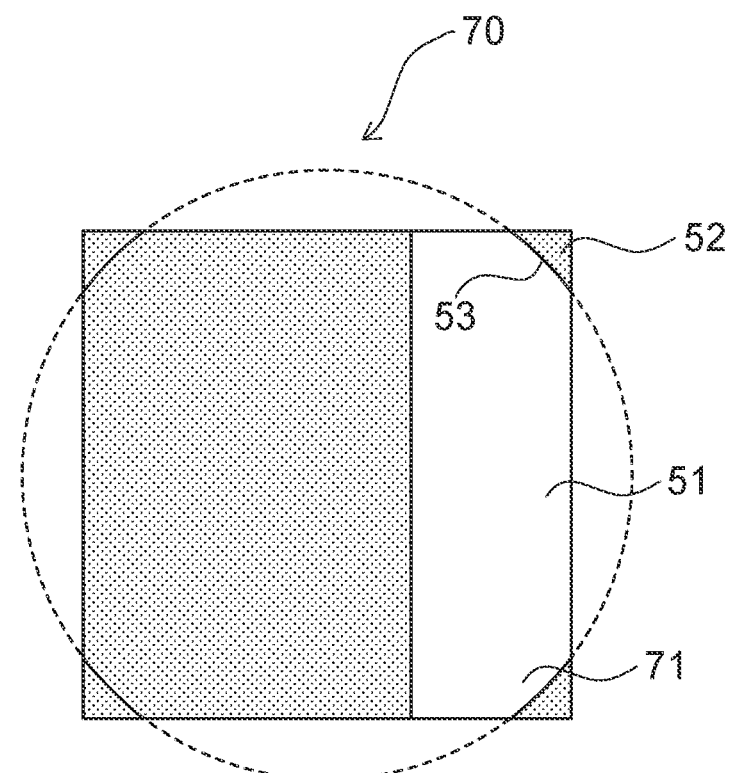

Examples of the area having uniform brightness are shown in FIG. 12A and FIG. 12B. FIG. 12A is a diagram showing a first example of an image which includes an outer edge. FIG. 12B is a diagram of a second example of an image which includes an outer edge.

In an image 60 which includes the outer edge of the first example, a shape of an area 61 having uniform brightness is an annular shape. Even with such shape, the area 61 having uniform brightness makes a contact with an outer edge 53 at four locations. Accordingly, it is possible to identify the outer edge 53 clearly.

The annular area can be obtained as described below. In the structure 40, two areas of mutually different reflectance are formed on the inner surface 44. Moreover, an area having a lower reflectance is located near a center of the inner surface 44.

In the structure 50, a light-shielding member is disposed on the light-emitting surface 51. Moreover, an opening having an annular shape is formed in the light-shielding member. Or, the light-emitting surface 51 is formed of a plurality of light sources. Furthermore, only light sources corresponding to the annular shape are made to emit light.

In an image 70 which includes the outer edge of the second example, a shape of an area 71 having uniform brightness is a substantially rectangular shape. Even with such shape, the area 71 having uniform brightness makes a contact with the outer edge 53 at two locations. Therefore, it is possible to identify the outer edge 53 clearly. It is possible to achieve the area having a substantially rectangular shape by making a same arrangement as in the first example.

The image sensor will be described below. In a case of one image sensor, the first imaging area and the second imaging area are formed in a single image pickup area.

In the image display apparatus 1, one image sensor 7 is used as shown in FIG. 2. The image sensor 7 includes the predetermined image pickup area 15 as the single image pickup area. The first imaging area 11 and the second imaging area 12 are formed in the predetermined image pickup area 15.

The predetermined image pickup area 15 includes the first image pickup area 16 and the second image pickup area 17. The first imaging area 11 is located in the first image pickup area 16. The second imaging area 12 is located in the second image pickup area 17.

A case of two image sensors will be described below. In the case of two image sensors, the first imaging area is located in an image pickup area of one image sensor and the second imaging area is located in an image pickup area of the other image sensor.

Figure 13A:
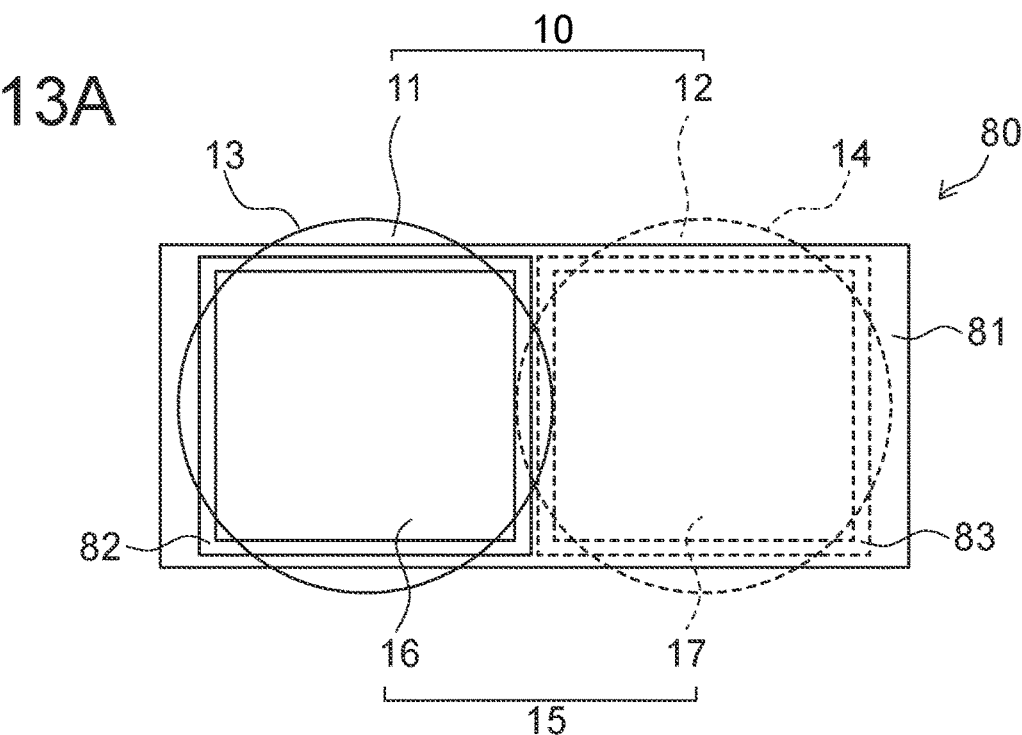
FIG. 13A and FIG. 13B are diagrams showing an example in which two image sensors are used.
Figure 13B:
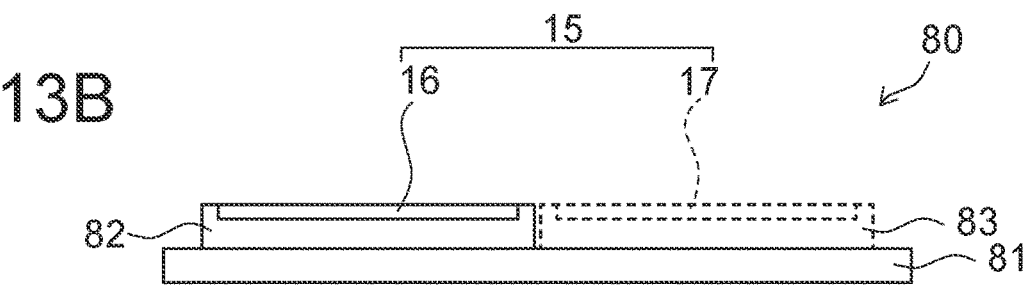

An example in which two image sensors are used is shown in FIG. 13A and FIG. 13B. FIG. 13A is a top view of an image pickup portion. FIG. 13B is a side view of the image pickup portion.

An image pickup portion 80 includes a substrate 81, a first image sensor 82, and a second image sensor 83. The first image sensor 82 and the second image sensor 83 are fixed to the single substrate 81.

The first image sensor 82 has the first image pickup area 16. The imaging area 11 is located on the first image pickup area 16. The second image sensor 83 has the second image pickup area 17. The second imaging area 12 is located on the second image pickup area 11.

The image pickup portion 80, similarly as the image sensor 7, has the first image pickup area 16 and the second image pickup area 17. Moreover, the first image sensor 82 and the second image sensor 83 are fixed to the single substrate 81. In this case, a shift in positions which is same as a shift in positions occurred between the image sensor 7 and the predetermined imaging area occurs between the image pickup portion 80 and the predetermined imaging area. Therefore, even by using the image pickup portion 80, it is possible to calculate the amount of shift.

In an image display method of the present embodiment, an image of an outer edge of a first imaging area is generated, an image of an outer edge of a second imaging area is generated, a feature point of the first imaging area is extracted on the basis of the image of the outer edge of the first imaging area, a feature point of the second imaging area is extracted on the basis of the image of the outer edge of the second imaging area, an amount of shift between a predetermined imaging area and an image sensor is calculated from the feature point of the first imaging area, the feature point of the second imaging area, and reference data, and a display position of a first image acquired from the first imaging area and a display position of a second image acquired from the second imaging area are determined from the amount of shift. The predetermined imaging area is formed on the image sensor, the predetermined imaging area includes the first imaging area and the second imaging area, the reference data includes data indicating a reference point in the predetermined area or data indicating a reference point in the predetermined image pickup area, and both the first imaging area and the second imaging area are images of a field of view of the objective optical system.

According to the image display method of the present embodiment, even when a position shift occurs between the image sensor and the optical system, it is possible to acquire a natural combined image.

Figure 14:
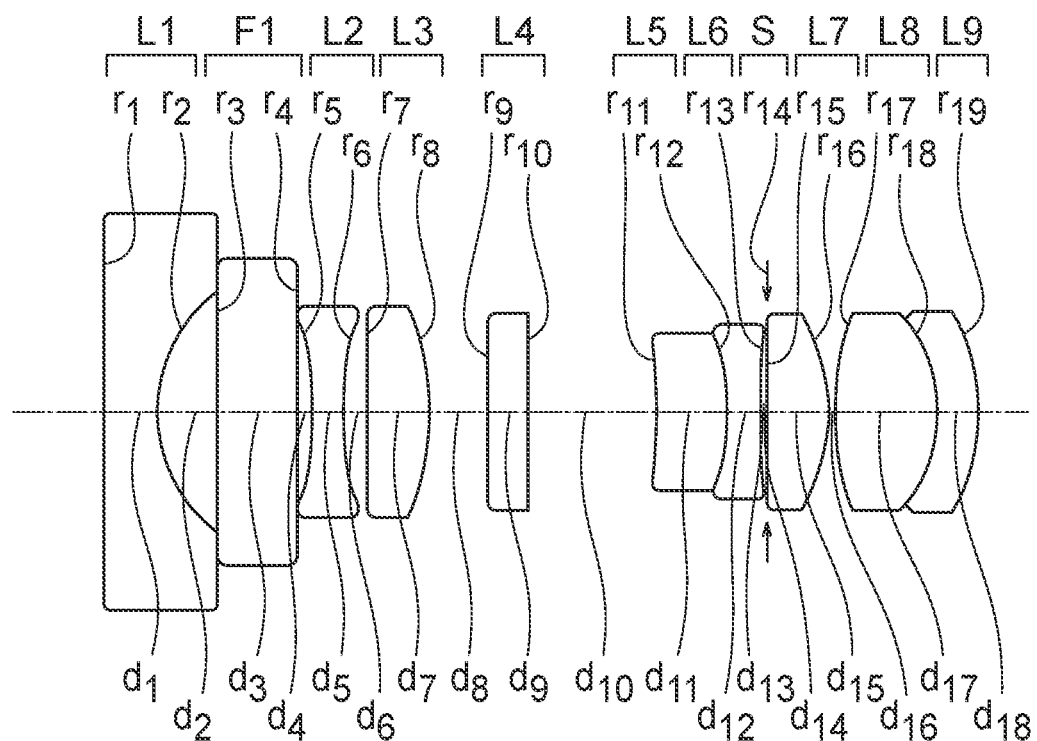
FIG. 14 is a diagram showing an example of an objective optical system.

An example of the objective optical system is shown in FIG. 14. An optical system includes a planoconcave negative lens L1, a biconcave negative lens L2, a biconvex positive lens L3, a planoconcave negative lens L4, a positive meniscus lens L5 having a convex surface directed toward an image side, a biconcave negative lens L6, a planoconvex positive lens L7, a biconvex positive lens L8, and a negative meniscus lens L9 having a convex surfaced directed toward the image side.

The positive meniscus lens L5 and the biconcave negative lens L6 are cemented. Moreover, the biconvex positive lens L8 and the negative meniscus lens L9 are cemented.

An optical filter F1 is disposed between the planoconcave negative lens L1 and the biconcave negative lens L2. Moreover, an aperture stop S is disposed between the biconcave negative lens L6 and the planoconvex positive lens L7.

Numerical data of an example described above is shown below. In symbols, r denotes radius of curvature of each surface, d denotes a thickness of each optical member or air distance, nd denotes a refractive index of each optical member for d-line, vd denotes an Abbe number for each optical member. In Various data, f denotes a focal length.

Example

| Surface no. | r | d | nd | vd |
|---|---|---|---|---|
| Object plane | ∞ | d0 | | |
| 1 | ∞ | 0.6561 | 1.88300 | 40.76 |
| 2 | 1.9220 | 0.8049 | | |

-continued

| | | | | |
|---|---|---|---|---|
| 3 | ∞ | 0.9841 | 1.51800 | 75.00 |
| 4 | ∞ | 0.1698 | | |
| 5 | −5.6263 | 0.3856 | 1.88300 | 40.76 |
| 6 | 3.3960 | 0.3075 | | |
| 7 | 93.7165 | 0.7666 | 1.92286 | 18.90 |
| 8 | −3.7545 | 0.7132 | | |
| 9 | −79.2437 | 0.4920 | 1.51633 | 64.14 |
| 10 | ∞ | 1.5581 | | |
| 11 | −62.7030 | 0.878 | 1.92286 | 18.90 |
| 12 | −2.8707 | 0.4100 | 2.00330 | 28.27 |
| 13 | 8.2363 | 0.0328 | | |
| 14(Stop) | ∞ | 0.0492 | | |
| 15 | ∞ | 0.7784 | 1.48749 | 70.23 |
| 16 | −2.3726 | 0.0820 | | |
| 17 | 3.6087 | 1.2486 | 1.48749 | 70.23 |
| 18 | −1.8711 | 0.4920 | 1.92286 | 18.90 |
| 19 | −2.9189 | | | |

| Various data | |
|---|---|
| f | 1 |
| Imh | 1 |
| Id | 1.18 |
| Iv | 0.74 |
| Ih | 0.92 |

The following arrangements may be made in the image display apparatus of the present embodiment. The embodiments below are also included in the present disclosure.

At least a part of the outer edge is a part of the circumference.

At least a part of the outer edge is a curve.

At least a part of the outer edge is a part of an elliptical circumference.

The feature point of the first area is a center of gravity of the first area or a center of the first area.

The feature point of the second area is a center of gravity of the second area or a center of the second area.

A part of the outer edge of the first imaging area is located in the predetermined image pickup area.

The entire outer edge of the first imaging area is located in the predetermined image pickup area.

A part of the outer edge of the second imaging area is located in the predetermined image pickup area.

The entire outer edge of the second imaging area is located in the predetermined image pickup area.

The area having uniform brightness is an area formed by light incident on the objective optical system, and the incident light is light reflected from an object surface, and the object surface has an area having a substantially uniform reflectance.

The area having uniform brightness is an area formed by light incident on the objective optical system, and the incident light is light emitted from a light source, and the light source has an area having a substantially uniform brightness distribution.

The number of image sensors is one, and the first imaging area and the second imaging area are located in the single image pickup area.

The number of image sensors is two, and the first imaging area is located in an image pickup area of one image sensor, and the second imaging area is located in an image pickup area of the other image sensor.

According to the present disclosure, it is possible to provide an image generation apparatus which enables to acquire easily a natural combined image even when a position shift occurs between the image sensor and the optical image, an image display apparatus, and an image display method.

As described heretofore, the present disclosure is suitable for an image generation apparatus which enables to acquire easily a natural combined image even when a position shift occurs between the image sensor and the optical image, an image display apparatus, and an image display method.

What is claimed is:

1. An image generation apparatus comprising:
an image pickup unit including (i) an objective optical system having one optical path, (ii) an optical-path splitter which physically splits the one optical path of the objective optical system into a first optical path and a second optical path, (iii) and an image sensor; and
an image processor,
wherein:
a predetermined imaging area is formed on the image sensor by the optical-path splitter,
the predetermined imaging area includes a first imaging area located in the first optical path and a second imaging area located in the second optical path,
both the first imaging area and the second imaging area are images of a field of view of the objective optical system,
both an outer edge of the first imaging area and an outer edge of the second imaging area are located at an inner side of a predetermined image pickup area of the image sensor,
an image of the outer edge of the first imaging area located in the predetermined image pickup area and an image of the outer edge of the second imaging area located in the predetermined image pickup area are captured by the image sensor,
the image processor has reference data,
the reference data includes one of data indicating a reference point in the predetermined imaging area and data indicating a reference point in the predetermined image pickup area, and
the image processor is configured to:
extract a feature point of the first imaging area based on the outer edge of the first imaging area, and extract a feature point of the second imaging area based on the outer edge of the second imaging area,
calculate an amount of shift between the predetermined imaging area and the image sensor using (i) at least one of the feature point of the first imaging area and the feature point of the second imaging area, and (ii) the reference data, and
determine, from the amount of shift, a display position of a first image acquired from the first imaging area and a display position of a second image acquired from the second imaging area.

2. The image generation apparatus according to claim 1, wherein:
the predetermined image pickup area includes a first image pickup area and a second image pickup area,
both the first image pickup area and the second image pickup area are rectangular-shaped areas,
the first imaging area is located in the first image pickup area,
the second imaging area is located in the second image pickup area, and
following conditional expressions (1) and (2) are satisfied:

$$1 < f/IH\max < 1.2 \quad (1),$$

$$0.8 < f/Id < 0.98 \quad (2)$$

where:
f denotes a focal length of the objective optical system,
IHmax denotes a maximum length in an area for display, and $$Id = \{(Iv/2)^2 + (Ih/2)^2\}^{1/2},$$

where:
Iv denotes a length in a longitudinal direction of the rectangular-shaped area, and
Ih denotes a length in a transverse direction of the rectangular-shaped area,
the area for display is an image pickup area located at an inner side of the first image pickup area and is used for display of the first image, or an image pickup area located at an inner side of the second image pickup area and is used for display of the second image, and
the maximum length is a maximum distance of distances from a center of the area for display to an outer edge of the area for display.

3. The image generation apparatus according to claim 1, wherein:
each of the image of the outer edge of the first imaging area located in the predetermined image pickup area and the image of the outer edge of the second imaging area located in the predetermined image pickup area has an inner-side area and an outer-side area,
the inner-side area is located at an inner side of the outer edge located in the predetermined image pickup area,
the outer-side area is located at an outer side of the outer edge located in the predetermined image pickup area,
the inner-side area includes an area having uniform brightness, and
the area having uniform brightness makes a contact with the outer edge located in the predetermined image pickup area.

4. An image display apparatus comprising:
an image generation apparatus according to claim 1; and
a display.

5. An image display method, comprising:
generating an image of an outer edge of a first imaging area captured by an image sensor that is included in an image-pickup unit;
generating an image of an outer edge of a second imaging area captured by the image sensor;
extracting a feature point of the first imaging area based on the image of the outer edge of the first imaging area, and extracting a feature point of the second imaging area based on the image of the outer edge of the second imaging area;
calculating an amount of shift between a predetermined imaging area and the image sensor using (i) at least one of the feature point of the first imaging area and the feature point of the second imaging area, and (ii) reference data; and
determining a display position of a first image acquired from the first imaging area and a display position of a second image acquired from the second imaging area, from the amount of shift;
wherein:
the image pickup unit includes (i) an objective optical system having one optical path, (ii) an optical-path splitter which physically splits the one optical path of the objective optical system into a first optical path and a second optical path, and (iii) the image sensor;

the predetermined imaging area is formed on the image sensor by the optical path-splitter, the predetermined imaging area includes the first imaging area which is located in the first optical path and the second imaging area which is located in the second optical path, both an outer edge of the first imaging area and an outer edge of the second imaging area are located at an inner side of a predetermined image pickup area of the image sensor, the reference data includes data indicating a reference point in the predetermined imaging area or data indicating a reference point in the predetermined image pickup area, and both the first imaging area and the second imaging area are images of a field of view of the objective optical system.

* * * * *